United States Patent [19]

Axen

[11] 4,065,633
[45] Dec. 27, 1977

[54] 2,2-DIFLUORO-13,14-DIHYDRO-PGA$_1$ ANALOGS

[75] Inventor: Udo F. Axen, Plainwell, Mich.

[73] Assignee: The Upjohn Company, Kalamazoo, Mich.

[21] Appl. No.: 724,155

[22] Filed: Sept. 17, 1976

Related U.S. Application Data

[62] Division of Ser. No. 552,708, Feb. 24, 1975, Pat. No. 4,001,300.

[51] Int. Cl.$^2$ .............................................. C07C 177/00
[52] U.S. Cl. .................................... 560/121; 260/404; 260/408; 260/514 D
[58] Field of Search ....................... 260/468 D, 514 D

[56] References Cited

U.S. PATENT DOCUMENTS

| | | | |
|---|---|---|---|
| 3,847,967 | 12/1974 | Lincoln et al. | 260/468 |
| 3,919,286 | 12/1975 | Bundy et al. | 260/468 |
| 3,962,293 | 6/1976 | Magerlin | 260/408 |

OTHER PUBLICATIONS

Burger, Medicinal Chemistry, pp. 81, 82 (1960).

*Primary Examiner*—Robert Gerstl
*Attorney, Agent, or Firm*—Robert A. Armitage

[57] ABSTRACT

2,2-Difluoro prostaglandin E, F$_\alpha$, F$_\beta$, A, and B analogs are disclosed with intermediates and with processes for making them. These compounds differ from the prostaglandins in that they have two fluoro atoms at the C-2 position in place of the two hydrogen atoms at C-2 in the prostaglandins. These compounds are useful for a variety of pharmacological purposes, including anti-ulcer, inhibition of platelet aggregation, increase in nasal patency, labor induction at term, and wound healing.

18 Claims, No Drawings

2,2-DIFLUORO-13,14-DIHYDRO-PGA₁ ANALOGS

The present application is a divisional application of Ser. No. 552,708, filed Feb. 24, 1975, now issued as U.S. Pat. No. 4,001,300, on Jan. 4, 1977.

The present invention relates to prostaglandin analogs for which the essential material constituting a disclosure therefor is incorporated by reference here from U.S. Pat. No. 4,001,300, issued Jan. 4, 1977.

I claim:

1. A compound of the formula

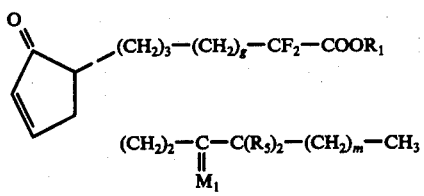

or a mixture comprising that compound and the enantiomer thereof, wherein $g$ is 2 to 4, inclusive;
wherein $M_1$ is

wherein $R_7$ and $R_8$ are hydrogen or methyl, with the proviso that one of $R_7$ or $R_8$ is methyl only when the other is hydrogen;
wherein $m$ is 2 to 4, inclusive;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro, alkyl of one to 4 carbon atoms, inclusive, or a pharmacologically acceptable cation,

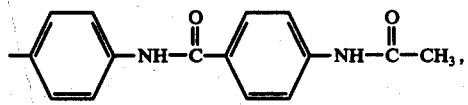

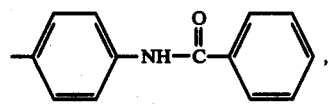

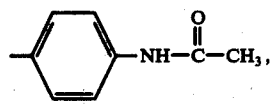

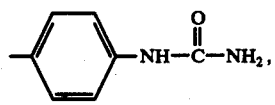

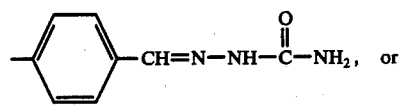

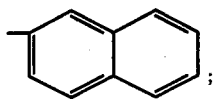

wherein
$R_5$ is hydrogen, methyl, or fluoro with the proviso that $R_5$ is fluoro only when $R_7$ and $R_8$ are both hydrogen, and with the proviso that $R_5$ is hydrogen only when either one of $R_7$ and $R_8$ is methyl.

2. A compound according to claim 1, wherein $M_1$ is

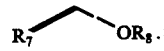

3. A compound according to claim 2, wherein $g$ is 2.
4. A compound according to claim 3, wherein $m$ is 3.
5. A compound according to claim 4, wherein $R_7$ is methyl.
6. 2,2-Difluoro-15-methyl-13,14-dihydro-PGA₁, a compound according to claim 5, wherein $R_1$ is hydrogen.
7. 2,2-Difluoro-15-methyl-13,14-dihydro-PGA₁, methyl ester, a compound according to claim 5, wherein $R_1$ is methyl.
8. A compound according to claim 4, wherein $R_8$ is methyl.
9. 2,2-Difluoro-13,14-dihydro-PGA₁, 15-methyl ether, a compound according to claim 8, wherein $R_1$ is hydrogen.
10. 2,2-Difluoro-13,14-dihydro-PGA₁, 15-methyl ether, methyl ester, a compound according to claim 8, wherein $R_1$ is methyl.
11. A compound according to claim 4, wherein $R_7$ and $R_8$ are hydrogen.
12. A compound according to claim 11, wherein $R_5$ is methyl.
13. 2,2-Difluoro-16,16-dimethyl-13,14-dihydro-PGA₁, methyl ester, a compound according to claim 12, wherein $R_1$ is methyl.
14. 2,2-Difluoro-16,16-dimethyl-13,14-dihydro-PGA₁, methyl ester, a compound according to claim 12, wherein $R_1$ is methyl.
15. A compound according to claim 11, wherein $R_5$ is fluoro.
16. 2,2,16,16-Tetrafluoro-13,14-dihydro-PGA₁, a compound according to claim 15, wherein $R_1$ is hydrogen.
17. 2,2,16,16-Tetrafluoro-13,14-dihydro-PGA₁, methyl ester, a compound according to claim 15, wherein $R_1$ is methyl.
18. The compound according to claim 1, wherein $M_1$ is

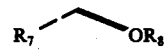

* * * * *

UNITED STATES PATENT OFFICE
CERTIFICATE OF CORRECTION

Patent No. 4,065,633     Dated December 27, 1977

Inventor(s) Udo F. Axen

It is certified that error appears in the above-identified patent and that said Letters Patent are hereby corrected as shown below:

Column 1, that portion of the formula on lines 19-20 should read

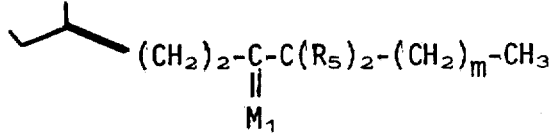

Column 2, line 16, should read -- hydrogen, with the proviso that $R_5$ is methyl only when $R_7$ and $R_8$ are both hydrogen, and with the proviso that $R_5$ is hydrogen --.

Signed and Sealed this

*Twentieth* Day of *June 1978*

[SEAL]

*Attest:*

RUTH C. MASON
*Attesting Officer*

DONALD W. BANNER
*Commissioner of Patents and Trademarks*